(12) United States Patent
Tegels

(10) Patent No.: US 9,980,719 B2
(45) Date of Patent: May 29, 2018

(54) NON-INVASIVE SUTURE CUTTER AND RELATED METHODS FOR CUTTING A SUTURE BELOW THE SKIN

(71) Applicant: ST. JUDE MEDICAL PUERTO RICO LLC, Caguas, PR (US)

(72) Inventor: Zachary J. Tegels, Minneapolis, MN (US)

(73) Assignee: St. Jude Medical Puerto Rico LLC, Caguas, PR (US)

( * ) Notice: Subject to any disclaimer, the term of this patent is extended or adjusted under 35 U.S.C. 154(b) by 1166 days.

(21) Appl. No.: 13/796,411

(22) Filed: Mar. 12, 2013

(65) Prior Publication Data

US 2014/0276973 A1  Sep. 18, 2014

(51) Int. Cl.
*A61B 17/04* (2006.01)
*A61B 17/00* (2006.01)
*A61B 90/00* (2016.01)

(52) U.S. Cl.
CPC ...... *A61B 17/0467* (2013.01); *A61B 17/0057* (2013.01); *A61B 2017/00654* (2013.01); *A61B 2017/00659* (2013.01); *A61B 2090/08021* (2016.02)

(58) Field of Classification Search
CPC ...... A24F 13/24; A24F 13/26; A61B 17/0057; A61B 17/0467; A61B 17/32; A61B 17/3209; A61B 17/32093; A61B 17/3211; A61B 2017/00637; A61B 2017/32113; A61B 2090/0801; A61B 2090/08021; A61B 2017/00654; A61B 2017/00659; B23D 59/006
See application file for complete search history.

(56) References Cited

U.S. PATENT DOCUMENTS

| | | | | |
|---|---|---|---|---|
| 173,915 | A * | 2/1876 | Deutsch et al. | A24F 13/24 30/109 |
| 3,802,074 | A * | 4/1974 | Hoppe | A61B 17/0467 30/134 |
| 5,405,351 | A * | 4/1995 | Kinet | A61B 17/0467 606/113 |
| 5,860,993 | A * | 1/1999 | Thompson | A61B 17/0467 30/151 |
| 6,254,620 | B1 * | 7/2001 | Koh | A61B 17/0467 30/278 |
| 7,094,246 | B2 * | 8/2006 | Anderson | A61B 17/0485 606/139 |
| 7,473,260 | B2 * | 1/2009 | Opolski | A61B 17/0467 606/148 |
| 7,618,436 | B2 | 11/2009 | Forsberg | |
| 7,618,438 | B2 | 11/2009 | White et al. | |
| 7,931,670 | B2 | 4/2011 | Fiehler et al. | |
| 8,109,945 | B2 * | 2/2012 | Boehlke | A61B 17/0057 606/148 |

(Continued)

*Primary Examiner* — Ryan J Severson
(74) *Attorney, Agent, or Firm* — Dorsey & Whitney LLP

(57) ABSTRACT

A suture cutting device including a housing, a cutting member, a suture recess, and an actuator. The cutting member is positioned in the housing. The suture recess is formed in the housing and configured to releasably connect the housing to the suture. The actuator is accessible outside of the housing and operable to move the cutting member laterally relative to the suture within the housing from a first position out of contact with the suture to a second position cutting the suture.

14 Claims, 13 Drawing Sheets

(56) References Cited

U.S. PATENT DOCUMENTS

| | | | | |
|---|---|---|---|---|
| 8,465,512 B2* | 6/2013 | Rosenhan | .......... | A61B 17/0467 |
| | | | | 606/167 |
| 9,072,512 B2* | 7/2015 | Rosenhan | .......... | A61B 17/0467 |
| 9,078,631 B2* | 7/2015 | Tegels | ................ | A61B 17/0057 |
| 9,486,192 B2* | 11/2016 | Pipenhagen | ....... | A61B 17/0057 |
| 9,820,734 B2* | 11/2017 | Gittard | ............... | A61B 17/0467 |
| 2006/0178682 A1* | 8/2006 | Boehlke | ............. | A61B 17/0057 |
| | | | | 606/148 |
| 2011/0029012 A1* | 2/2011 | Tegels | ................ | A61B 17/0057 |
| | | | | 606/213 |
| 2012/0158045 A1* | 6/2012 | Pipenhagen | ....... | A61B 17/0057 |
| | | | | 606/213 |
| 2014/0276973 A1* | 9/2014 | Tegels | ................ | A61B 17/0467 |
| | | | | 606/144 |
| 2017/0035400 A1* | 2/2017 | Pipenhagen | ........ | A61B 17/0057 |

* cited by examiner

NON-INVASIVE SUTURE CUTTER AND RELATED METHODS FOR CUTTING A SUTURE BELOW THE SKIN

TECHNICAL FIELD

The present disclosure relates generally to medical devices, and more particularly to suture cutting devices and methods.

BACKGROUND

Various surgical procedures are routinely carried out intravascularly or intraluminally. For example, in the treatment of vascular disease, such as arteriosclerosis, it is a common practice to access the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., catheters) may pass through the sheath to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices.

Prior closure devices place a sealing plug at the tissue puncture site. Deployment of the sealing plug involves ejecting the plug from within a device sheath and compaction down to an outer surface of the tissue puncture using a compaction member. After the sealing plug has been compacted, the suture is manually cut by the operator at a location outside of the patient. There is a need for improving the mechanism and method for cutting a suture of the closure device after depositing and compacting the sealing plug.

SUMMARY

One aspect of the present disclosure relates to a suture cutting device including a housing, a cutting member, a suture recess, and an actuator. The cutting member is positioned in the housing. The suture recess is formed in the housing and configured to releasably connect the housing to the suture. The actuator is accessible outside of the housing and operable to move the cutting member laterally relative to the suture within the housing from a first position out of contact with the suture to a second position cutting the suture.

The suture cutting device may include a biasing member disposed between the cutting member and the housing and configured to bias the cutting member into the first position. The cutting member may include an elongate blade. The cutting member may include a contoured shape along its length. The housing may include a skin contact surface arranged to contact a skin surface through which the suture extends. The housing may include a tapered shape from a first end to a second end. The actuator may extend laterally from a sidewall of the housing. The cutting member may be arranged in the housing at an angle relative to the suture.

Another aspect of the present disclosure relates to a suture cutting device that includes a housing, a cutting member, and an actuator. The housing includes a housing interior and a suture connection feature configured to releasably connect the housing to a suture with the suture passing through the housing interior. The actuator is coupled to the cutting member and operable to move the cutting member within the housing interior to cut the suture.

The housing may include opposing first and second end walls, and the suture connection feature includes at least one suture recess formed in at least one of the first and second end walls. The at least one suture recess may be open in a lateral direction. The at least one suture recess may include a first suture recess formed in the first end wall and a second suture recess formed in the second end wall. The cutting member may include an elongate blade movable in a lateral direction relative to the suture. The actuator may include a first portion accessible along an exterior of the housing and a second portion coupled to the blade to move the blade along an axle within the housing.

Another aspect of the present disclosure relates to a method of cutting a suture extending from an incision in a tissue layer. The method includes providing a housing, a cutting member, and an actuator, wherein the housing has a skin contact surface. The method may also include releasably connecting the housing to the suture, pressing the skin contact surface of the housing against an outer surface of the tissue layer, and operating the actuator to move the cutting member within the housing to cut the suture.

Operating the actuator may include moving the cutting member in a lateral direction relative to the suture. The method may include arranging the cutting member within the housing at an angle relative to the suture. The method may include releasing the housing member from being pressed against the skin surface after cutting the suture to position a cut end of the suture within the incision beneath the outer surface of the tissue layer. Releasably connecting the housing to the suture may include laterally inserting the suture into at least one suture recess formed in the housing.

A further aspect of the present disclosure relates to an internal tissue puncture closure and cutting system that includes a closure device and a suture cutting device. The closure device is insertable into a tissue puncture and includes a suture, an anchor, a sealing plug, and a driving mechanism. The suture extends from a first end of the closure device to a second end of the closure device. The anchor is attached to the suture at the second end of the closure device. The sealing plug is slidingly attached to the suture at a position adjacent to the anchor. The driving mechanism is operable to compact the sealing plug toward the second end to seal the tissue puncture percutaneously. The suture cutting device is releasably connected to the suture after withdrawal of the closure device from the tissue puncture. The suture cutting device includes a housing and a cutting member operable in a lateral direction within the housing to cut the suture.

The housing may be configured to be pressed against an outer surface of a tissue layer adjacent to the tissue puncture through which the suture extends, and the suture cutting device may be operable to cut the suture below the outer surface of the tissue layer. The suture cutting device may include an actuator coupled to the suture cutting member, wherein the actuator is operable in a lateral direction relative to the housing to move the cutting member within the housing.

A further aspect of the present disclosure relates to a method of sealing a tissue puncture in an internal tissue wall accessible through a percutaneous incision. The method includes providing a suture cutting device and a tissue puncture closure device, wherein the suture cutting device includes a housing and a cutting member, and the tissue puncture closure device includes a suture, an anchor, a compaction member, and a sealing plug positioned proximal of the anchor. The suture is connected at its distal end to the anchor and the sealing plug. The method includes inserting the tissue puncture closure device into the percutaneous incision, deploying the anchor into the tissue puncture, compacting the sealing plug toward the anchor with the compaction member, connecting the suture to the suture cutting device, operating the cutting member to cut the suture within the housing, and depositing the anchor and the sealing plug at the tissue puncture.

The method may further include pressing the housing against an outer surface of the patient adjacent to the percutaneous incision prior to cutting the suture, wherein a free end of the suture after being cut is positioned within the incision after releasing the housing from being pressed against the outer surface. The method may include operating the cutting member to move the cutting member in a lateral direction relative to the suture. Connecting the suture to the suture cutting device may include laterally inserting the suture into at least one suture recess formed in the housing.

Additional advantages and novel features will be set forth in the description which follows or may be learned by those skilled in the art through reading these materials or practicing the examples disclosed herein.

BRIEF DESCRIPTION OF THE DRAWINGS

The accompanying drawings illustrate various embodiments of the present disclosure and are a part of the specification. The illustrated embodiments are merely examples and do not intend to be limiting.

Throughout the drawings, identical reference numbers designate similar, but not necessarily identical, elements.

DETAILED DESCRIPTION

Figure 1:
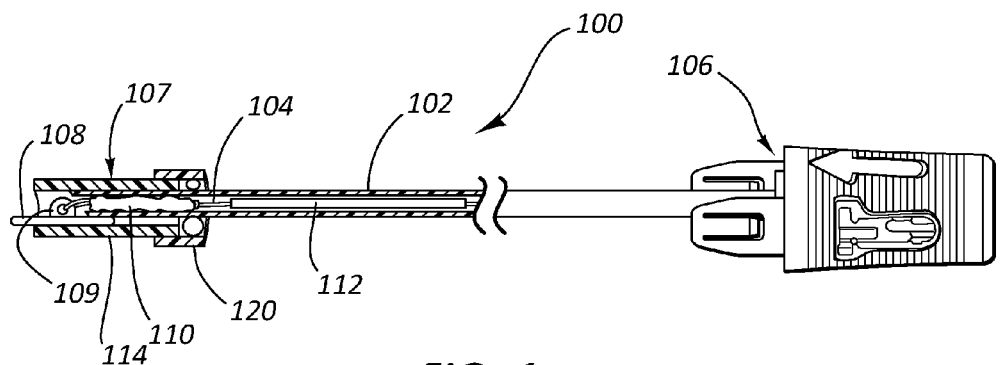
FIG. 1 is a perspective view of an example vascular closure device according to the present disclosure.

As mentioned above, vascular procedures are conducted throughout the world and require access to an artery through a puncture. Often, the artery is a femoral artery. To close the puncture following completion of the procedure, many times a closure device is used to sandwich the puncture between an anchor and a sealing plug. A suture is often used to couple together the anchor and sealing plug. A force may be applied along the suture to draw the anchor and sealing plug toward each other as the sealing plug is compressed against the puncture. Typically, the suture is manually cut at a location outside of the patient after confirmation that the puncture has been sealed. Cutting the suture releases the anchor and sealing plug from the remaining portions of the closure device. Leaving a length of suture protruding through the patient's skin surface may result in complications such as, for example, infections that may arise at a location where the suture exits the patient's skin. Further, requiring the extra step of manually cutting the suture with an instrument that is separate from the closure device typically requires three concurrent steps: 1) applying tension in the suture, 2) operating the cutting device, and 3) pressing down on the skin surface adjacent to the tissue puncture through which the suture extends. The step of pressing down on the skin surface may alleviate concerns about inadvertently dislodging the sealing plug and anchor when applying tension in the suture. Further, pressing down on the skin surface may be useful when attempting to cut the suture at a point below the skin surface. These three concurrent steps may be difficult to perform by a single person.

The present disclosure describes apparatuses and methods that facilitate cutting of the suture while minimizing potential harm to the patient during cutting. The present disclosure further describes apparatuses and methods that facilitate cutting of the suture within a percutaneous incision at a location below the patient's outer skin surface. The present disclosure further describes apparatuses and methods that may be performed by a single operator. While the vascular instruments shown and described below include procedure sheaths and puncture sealing devices, the application of principles described herein are not limited to the specific apparatuses shown. The principles described herein may be used with any medical device and any procedure that involves the use of a suture or other elongate filament that requires cutting. Therefore, while the description below is directed primarily to vascular procedures and certain embodiments of a vascular closure device, the methods and apparatuses are only limited by the appended claims.

The general structure and function of tissue closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

As used in this specification and the appended claims, the term "compact" or "compacting" is used broadly to mean any type of tamping (i.e., packing down by one or a succession of blows or taps or smooth, steady pressure, but not by excessive force), compacting, or compressing. "Engage" and "engagable" are also used broadly to mean interlock, mesh, or contact between two structures or devices. Likewise "disengage" or "disengageable" means to remove or capable of being removed from interlock, mesh, or contact. A "tube" is an elongated device with a passageway. The passageway may be enclosed or open (e.g., a trough). A "lumen" refers to any open space or cavity in a bodily organ, especially in a blood vessel. The words "including" and "having," as used in the specification, including the claims, have the same meaning as the word "comprising."

Referring to FIGS. 1-5, a vascular puncture closure device 100 is shown according to the prior art. Some example closure devices are disclosed in U.S. Pat. Nos. 7,618,436; 7,618,438; and 7,931,670, which patents are incorporated herein in their entireties by this reference. The closure device 100 includes a carrier tube 102 with a filament or suture 104 extending at least partially therethrough. The closure device 100 also includes a first or proximal end 106 and a second or distal end 107. An anchor 108 is positioned external to the second or distal end 107 of the carrier tube 102. The anchor may be elongated, stiff, low profile member having an eye 109 formed at the middle. The anchor 108 is typically made of a biologically resorbable polymer.

The suture 104 is threaded through the anchor 108 and back to a sealing plug 110, which may comprise collagen or other expandable, absorbent, bioresorbable materials. The sealing plug 110 may be comprised of randomly oriented fibrous material bound together by chemical means. The sealing plug 110 is slidingly attached to the suture 104 as the suture passes distally through the carrier tube 102, but as the suture traverses the anchor 108 and reenters the carrier tube 102, it is securely slip knotted proximal to the sealing plug 110 to facilitate cinching of the sealing plug 110 when the closure device 100 is properly placed and the anchor 108 deployed (see FIG. 4).

The carrier tube 102 typically includes a compaction member 112 disposed therein. The compaction member 112 is slidingly mounted on the suture 104 and may be used by an operator to compact the sealing plug 110 toward the anchor 108 at an appropriate time to seal a percutaneous tissue puncture.

Prior to deployment of the anchor 108 within an artery, the eye 109 of the anchor 108 rests outside the distal end 107 of the carrier tube 102. The anchor 108 may be temporarily held in place flush with the carrier tube 102 by a bypass tube 114 disposed over the distal end 107 of the carrier tube 102.

Figure 2:
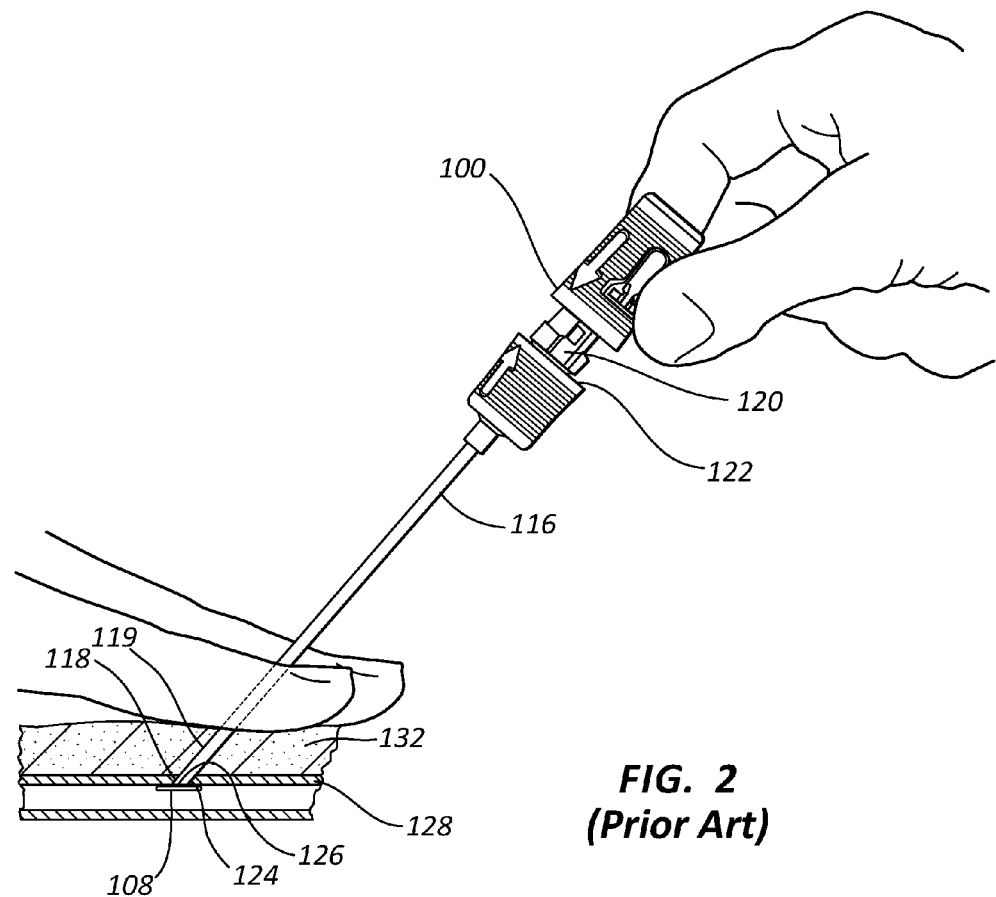
FIG. 2 is a perspective view of the vascular closure device shown in FIG. 1 with an anchor disposed in a vessel.
Figure 3:
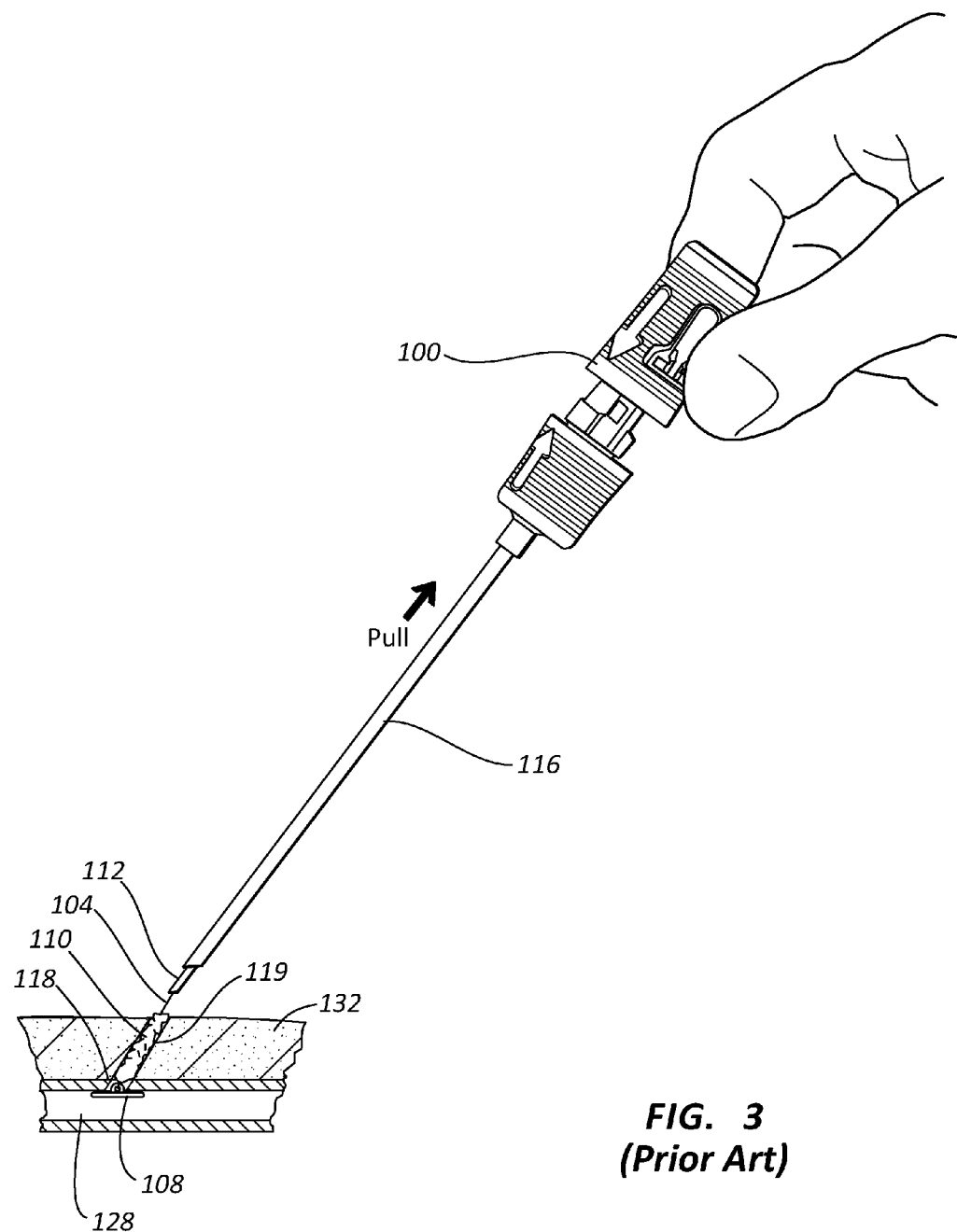
FIG. 3 is a perspective view of the vascular closure device shown in FIG. 1 with the sealing plug disposed in the percutaneous incision.
Figure 4:
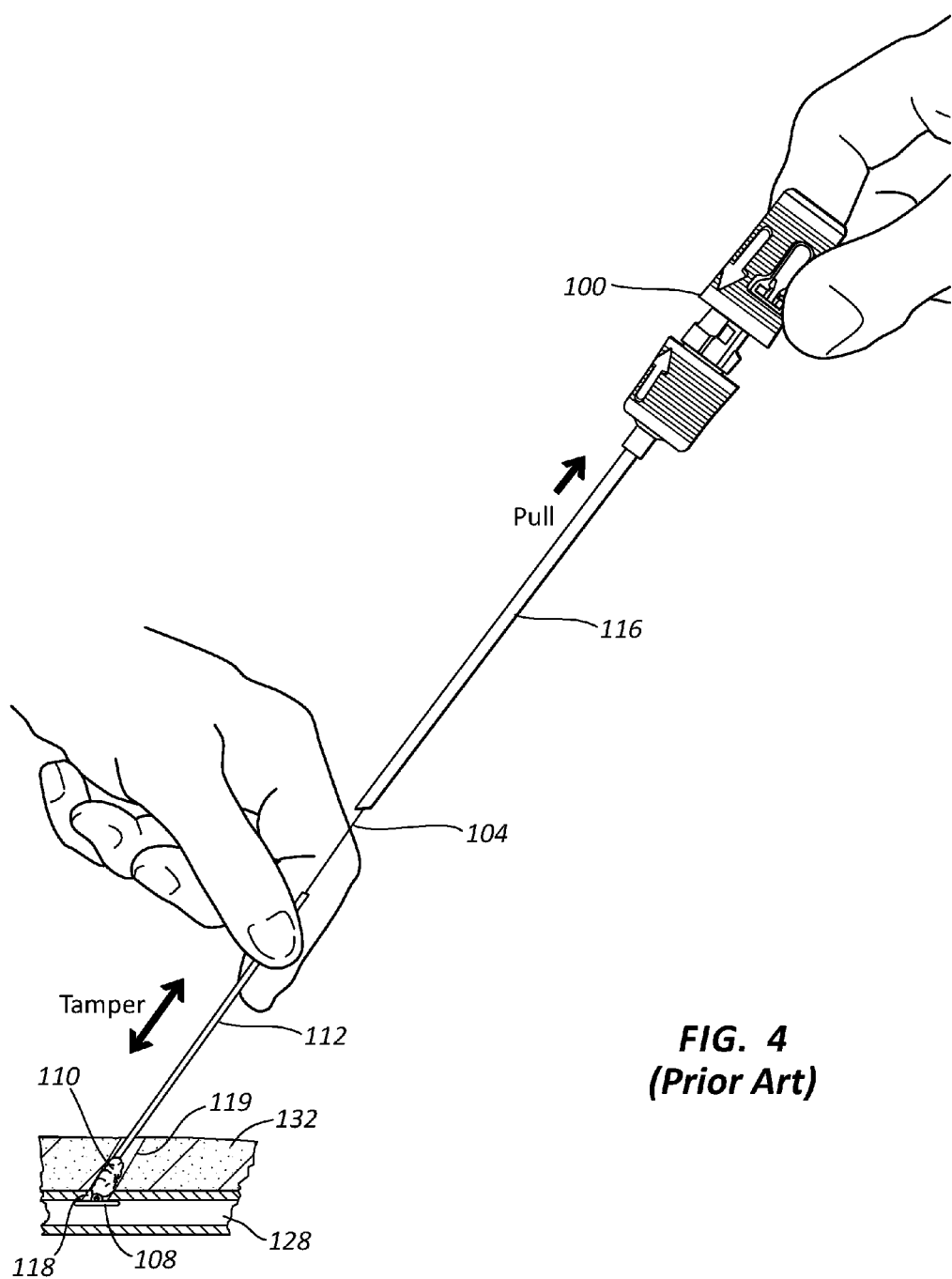
FIG. 4 is a perspective view of the vascular closure device shown in FIG. 1 with the operator compacting the sealing plug with a compaction member.

The flush arrangement of the anchor 108 and carrier tube 102 allows the anchor 108 to be inserted into a procedure sheath such as insertion sheath 116 as shown in FIGS. 2-4, and eventually through a tissue puncture 118. The insertion sheath 116 is shown in FIGS. 2-4 inserted through a percutaneous incision 119 in a tissue layer 132 and into an artery 128. However, the bypass tube 114 (see FIG. 1) includes an oversized head 120 that prevents the bypass tube 114 from passing through an internal passage of the insertion sheath 116. Therefore, as the closure device 100 is inserted into the insertion sheath 116, the oversized head 120 bears against a surface 122 of insertion sheath 116.

Further insertion of the closure device 100 results in sliding movement between the carrier tube 102 and the bypass tube 114, and releases the anchor 108 from the bypass tube 114. However, the anchor 108 remains in the flush arrangement shown in FIG. 1 following release from the bypass tube 114, limited in movement by the insertion sheath 116.

The insertion sheath 116 may include a monofold 124 at a second or distal end 126 thereof. The monofold 124 acts as a one-way valve to the anchor 108. The monofold 124 is a plastic deformation in a portion of the insertion sheath 116 that elastically flexes as the anchor 108 is pushed out through the distal end 126 of the insertion sheath 116. Typically, after the anchor 108 passes through the distal end 126 of the insertion sheath 116 and enters the artery 128, the anchor 108 is no longer constrained to the flush arrangement with respect to the carrier tube 102 and it deploys and rotates to the position shown in FIG. 2.

Referring next to FIGS. 3-4, with the anchor 108 deployed, the closure device 100 and the insertion sheath 116 are withdrawn together, ejecting the sealing plug 110 from the carrier tube 102 into the percutaneous incision 119 and exposing the compaction member 112. With the compaction member 112 fully exposed as shown in FIG. 4, the sealing plug 110 is manually compacted, and the anchor 108 and sealing plug 110 are cinched together and held in place with the self-tightening slip-knot on the suture 104. Thus, the tissue puncture is sandwiched between the anchor 108 and the sealing plug 110, thereby sealing the tissue puncture 118. The suture 104 is then cut and the percutaneous incision 119 may be closed. The suture 104, anchor 108, and sealing plug 110 are generally made of resorbable materials and therefore remain in place while the tissue puncture 118 heals.

Figure 5:
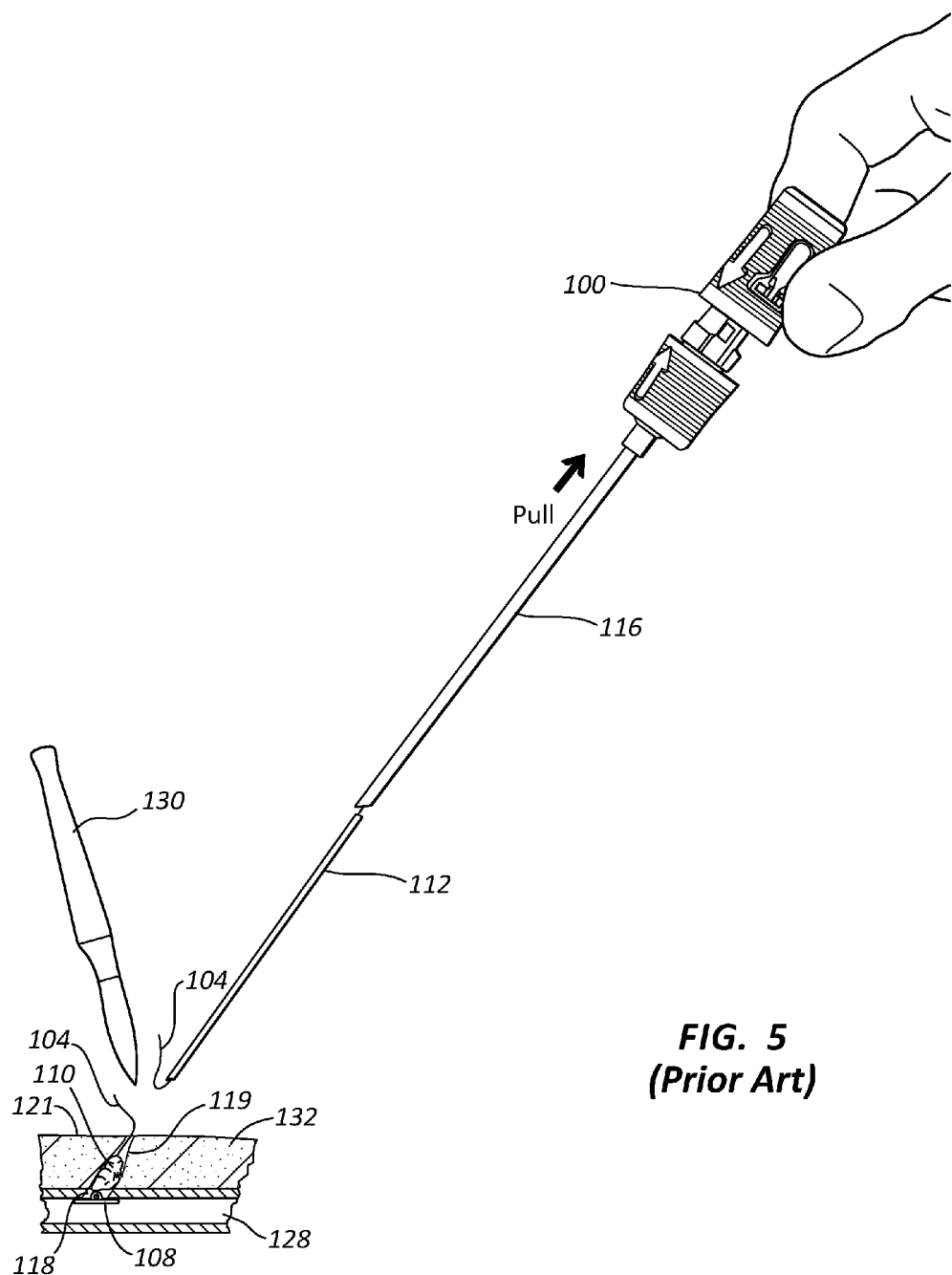
FIG. 5 is a perspective view of the vascular closure device shown in FIG. 1 with the operator manually cutting the suture at a location outside of the percutaneous incision.

FIG. 5 illustrates cutting of the suture 104 after compaction of the sealing plug 110 is completed. Typically, the suture 104 is cut using a suture cutting device 130, which is separate and distinct from the closure device 100. A free or cut end 105 of the suture 104 is located outside of the percutaneous incision 119. Thus, the suture 104 passes through an outer skin surface 121. Further, the suture cutting device 130 includes at least one cutting surface that is exposed for contacting the patient and operator as well as the suture 104. Attempts to cut the suture 104 at a location below the outer skin surface 121 by inserting the suture cutting device 130 into the percutaneous incision 119 may result in injury to the patient or the operator. Further, applying additional tension in the suture 104 while cutting the suture close to the skin surface 121 in an attempt to cut the suture 104 to a shorter length may displace the sealing plug 110.

The present disclosure relates to suture cutting devices operable to cut a suture. In some embodiments, the suture cutting device is operable to cut a suture below an outer surface of a tissue layer, such as a skin surface, with reduced risk of injuring the patient. The suture is preferably mounted to the cutting device at any point along the suture and able to slide along the suture to a desired cutting position. The suture cutting device includes a housing and a cutting member that is at least partially enclosed within the housing. The cutting member may be operable in a lateral direction relative to the suture to cut the suture. The cutting member may be operable using an actuator, which is accessible along an exterior of the suture cutting device, such as along a side surface of the housing. The actuator may move the cutting member along an axle arranged laterally through the housing. The cutting member may be supported within the housing to maintain a constant orientation relative to the housing while being moved along the axle. The cutting member may be biased into a first position out of contact with the suture, such that the cutting member does not unintentionally cut the suture until the operator actively operates the actuator. Furthermore, the cutting member may automatically return to the first position under force of the biasing member after operating the actuator to cut the suture.

Referring now to FIGS. 6-19, a suture cutting device 230 and its operation is shown and described according to one embodiment of the present disclosure. The suture cutting device 230 may have particular utility when used in connection with tissue puncture closure devices such as the closure device 100 described above. However, any suture cutting operation associated with any type of closure device may be accomplished with the suture cutting device 230.

Figure 6:
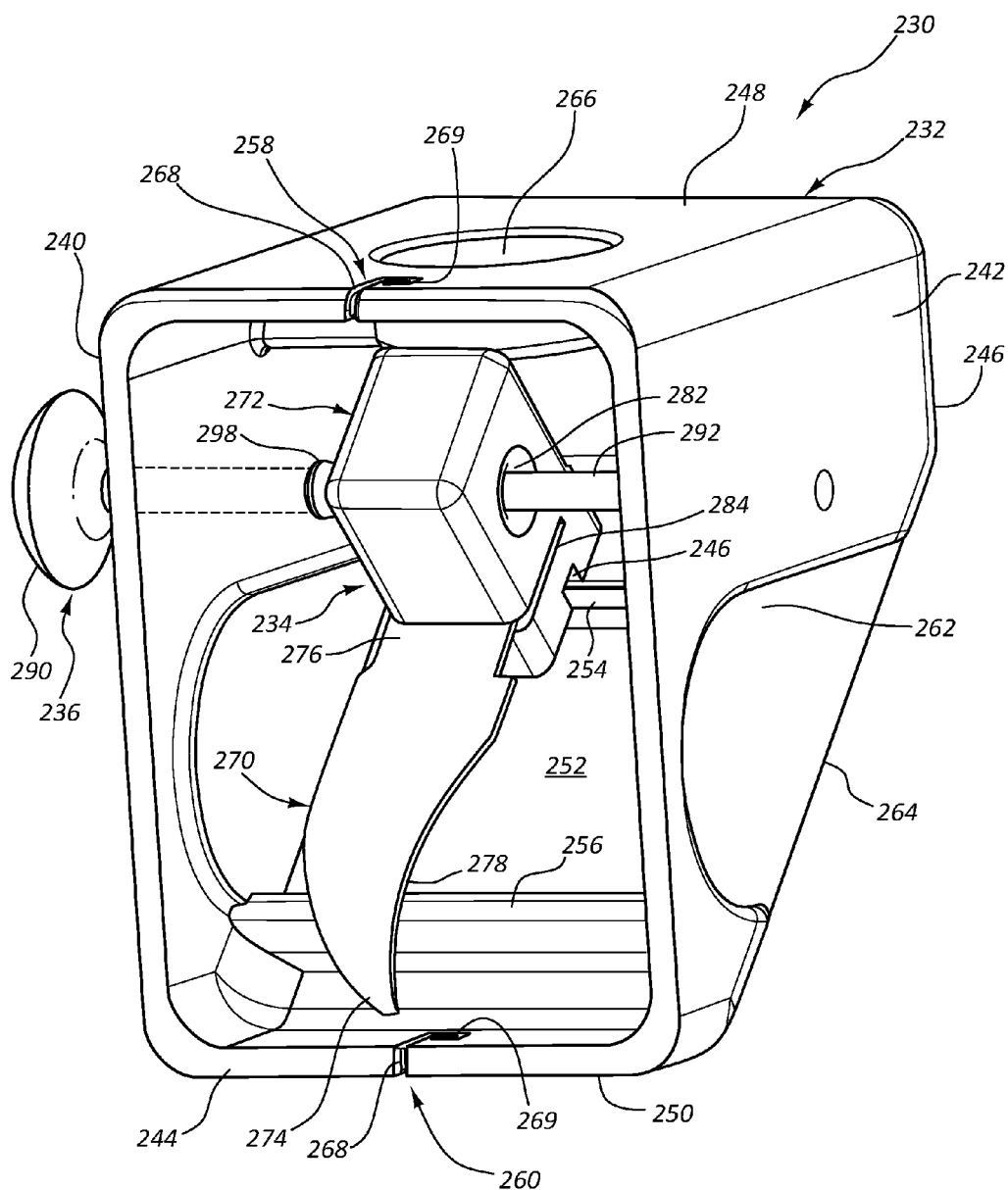
FIG. 6 is a perspective view of an example suture cutting device in accordance with the present disclosure.
Figure 7:
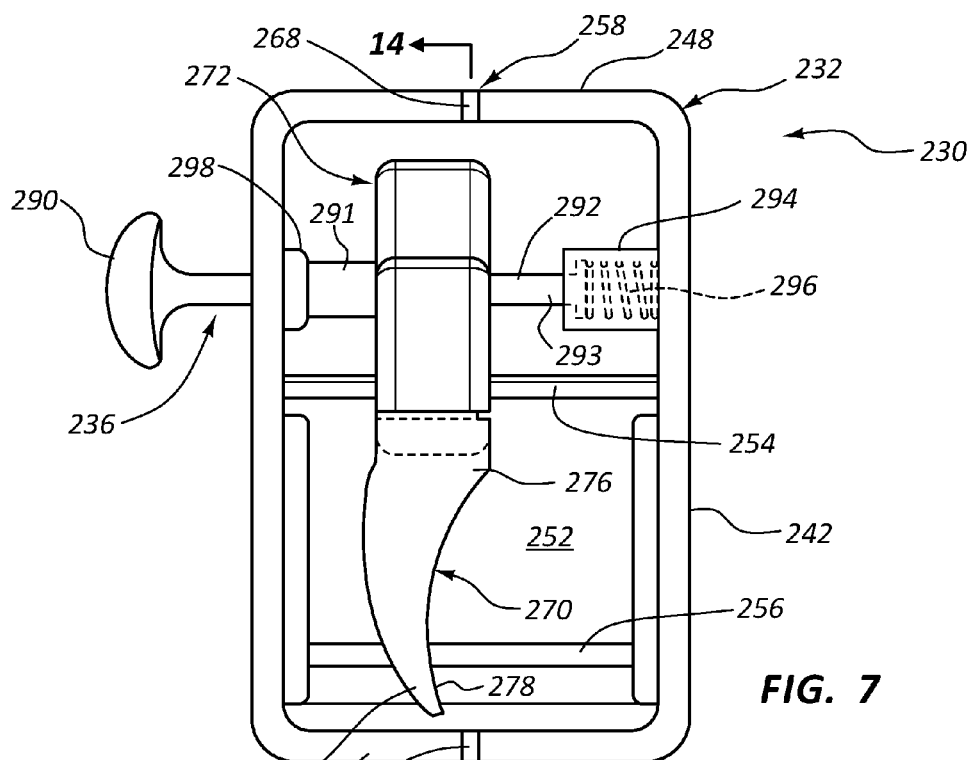
FIG. 7 is a front view of the suture cutting device of FIG. 6.

Referring first to FIGS. 6 and 7 (and FIGS. 6-14 generally), the suture cutting device 230 includes a housing 232, a cutting member assembly 234, and an actuator assembly 236. The cutting member assembly 234 is positioned within an interior of the housing 232. The actuator assembly 236 is operable to move the cutting member assembly 234 within the housing 232 to cut a suture that passes through the housing 232. A portion of the actuator assembly 236 may be accessible along an exterior of the housing 232 for access by an operator. The suture cutting device 230 may have a construction that permits operation using a single hand of an operator. The housing 232 may include a construction that is easy to grasp and hold by one hand of an operator while a finger or thumb of that same hand operates the actuator assembly. A portion of the housing 232 may assist in depressing an outer skin surface of the patient adjacent to a tissue puncture to help facilitate cutting the suture at a location below an outer skin surface.

The suture cutting device 230 may be configured to at least partially enclose a cutting member of the cutting member assembly 234 during operation of the suture cutting device 230. Enclosing the cutting member may limit exposure of the operator to the cutting member. Enclosing the cutting member may limit exposure of the outer skin surface or other anatomical features of the patient to the cutting member when cutting the suture.

The housing 232 includes first and second sides 240, 242, front and rear sides 244, 246, top and bottom ends 248, 250, an interior 252, an alignment track 254, a support member 256, and first and second suture recesses 258, 260. The first and second sides 240, 242 each include a recess 262. The recesses 262 may be sized to receive a thumb or finger of an operator's hand to assist in grasping the housing 232. The rear side 246 includes a tapered portion 264. The tapered portion 264 may also provide a reduced size for the housing 232 that provides easier grasping of the housing 232. The tapered portion 264 may also help minimize the size of the bottom end 250. The bottom end 250 includes a tissue contact surface along an exterior thereof that transfers a downward (e.g., vertical or perpendicular to an outer tissue surface) directed force to an outer skin surface adjacent to a tissue puncture prior to and during cutting of a suture as will be described in further detail below. The smaller the size of the bottom end 250, the easier it may be to depress the skin surface adjacent to the tissue puncture, which may lead to cutting of the suture deeper within the tissue puncture The first and second suture recesses 258, 260 may include a lateral entry portion 268 and a retention portion 269 (see FIG. 6). The lateral entry portion 268 may be sized and arranged for lateral insertion of a suture into the first and second suture recesses 258, 260. The retention portion 269 may include a cut back portion within which the suture resides to help retain the suture connected to the housing 232 while operating the actuator assembly 236 and moving the suture cutting device 230 axially along a length of the suture.

The first and second suture recesses 258, 260 may include a clip, tab, or other feature that provides a one-way entry into the retention portion 269 to further assist in maintaining a positive connection between the suture and the suture cutting device 230.

The front side 244 of the housing 232 may have a generally open construction that permits access to the cutting member assembly 234. Other constructions are possible for the housing 232 in which the front side 244 is generally covered while still providing the lateral access into the first and second suture recesses 258, 260 discussed above. Other exterior surfaces of the housing 232 may be closed or at least partially open to provide access to the cutting member assembly 234.

One or more of the first and second sides 240, 242, front and rear sides 244, 246, and top and bottom ends 248, 250 may be detachable from the housing 232 to provide access into the interior 252 as desired. Furthermore, any one of the first and second sides 240, 242, front and rear sides 244, 246, top and bottom ends 248, 250 may include a recess or other gripping feature such as a plurality of ridges or protrusions, the recess 262 described above with reference to the first and second sides, 240, 242, or a recess 266 formed in the top end 248.

The cutting member assembly 234 may include a cutting member 270 and a carrier 272. The cutting member 270 includes distal and proximal ends 274, 276 and a cutting surface 278. The carrier 272 may include a mounting slot 280, an axle bore 282, and a track slot 284. The proximal end 276 of the cutting member 270 is insertable into the mounting slot 280. The cutting member 270 may be retained in the mounting slot 280 using, for example, an interference fit, a fastener, or a bonding agent such as an adhesive. The axle bore 282 may be sized to receive a component of the actuator assembly 236 as will be described in further detail above below. The track slot 284 may receive the alignment track 254 to assist in holding the cutting member assembly 234 within the interior 252 of the housing while permitting lateral movement of the cutting member assembly 234 within the housing 232. The alignment track 254 may extend laterally across the housing 232 along, for example, an inner surface of the rear side 246 as shown in FIG. 6.

The distal end 274 of the cutting member 270 may be supported against the support member 256 as shown in FIG. 6. The cutting member 270 may slide along the support member 256 while the cutting member assembly 234 moves laterally within the housing 232. The support member 256 may be positioned along an interior surface of the housing 232 and extend laterally across a width of the housing 232. In one example, the support member 256 is positioned along an interior surface of the rear side 246 as shown in FIG. 6. The support member 256 may stabilize a position of the distal end 274 relative to the suture.

The cutting member 270 may have a generally elongate shape with a greater length than width, and a thickness that is substantially less than the width and length. The cutting member 270 may include a contoured shaped along its length. In one example, the cutting surface 278 is positioned along a concave portion of the distal end 274. Typically, a distal-most portion of the cutting member 270 includes a cutting surface such that the cutting member assembly 234 cuts the suture close to the bottom end 250 of the housing 232.

Figure 8:
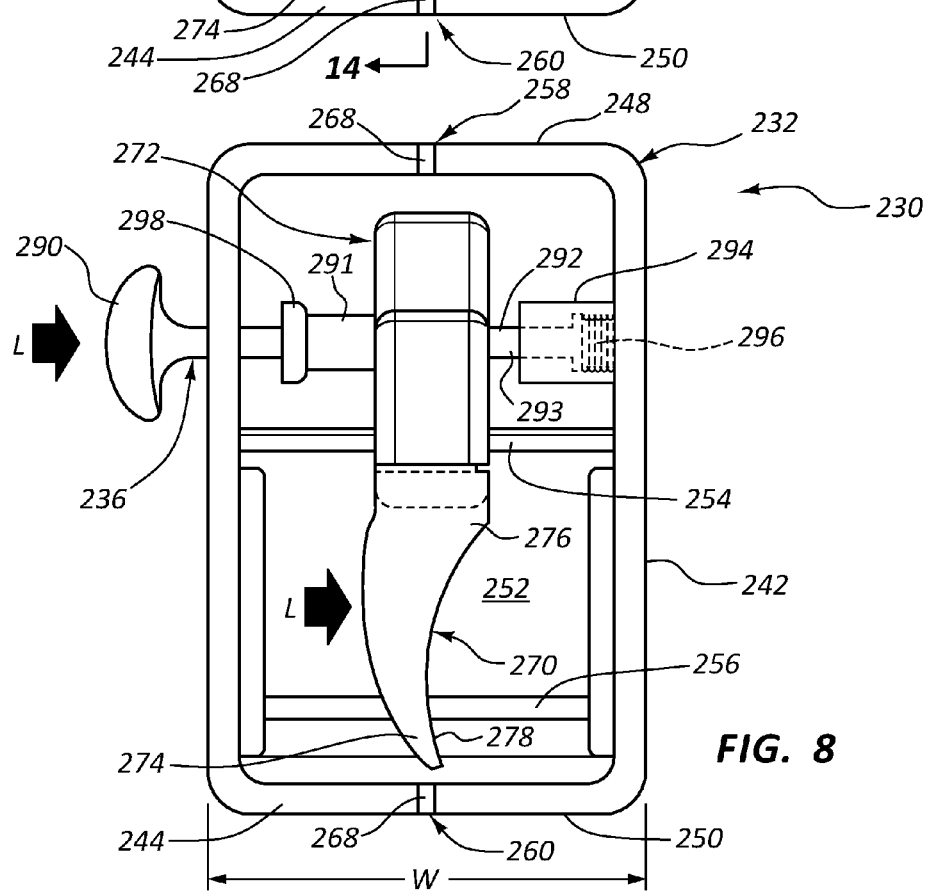
FIG. 8 is a front view of the suture cutting device of FIG. 6 in an actuated position.
Figure 9:
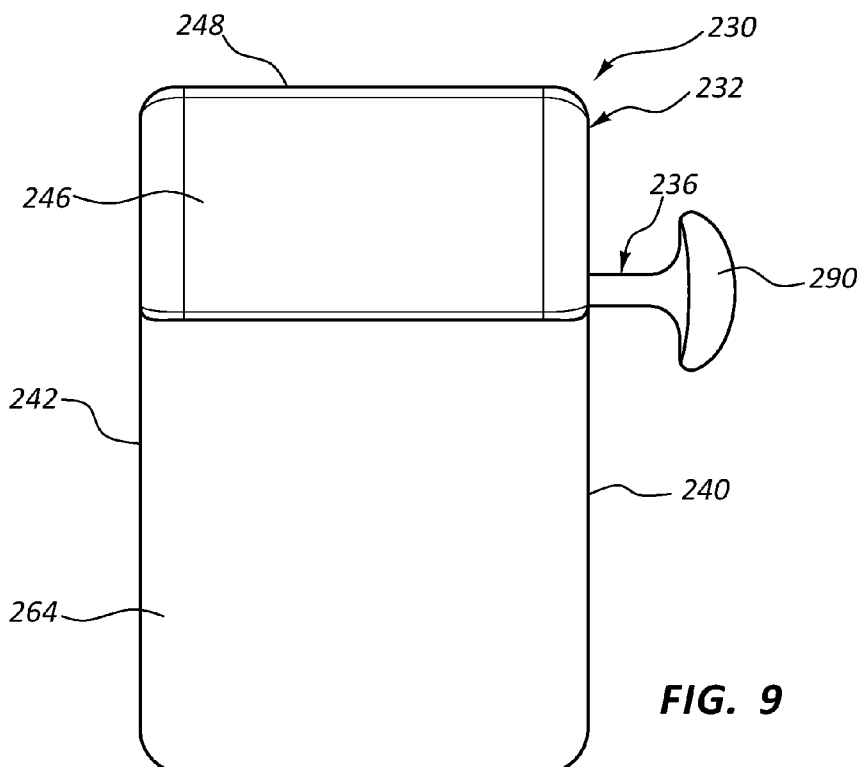
FIG. 9 is a rear view of the suture cutting device of FIG. 6.
Figure 10:
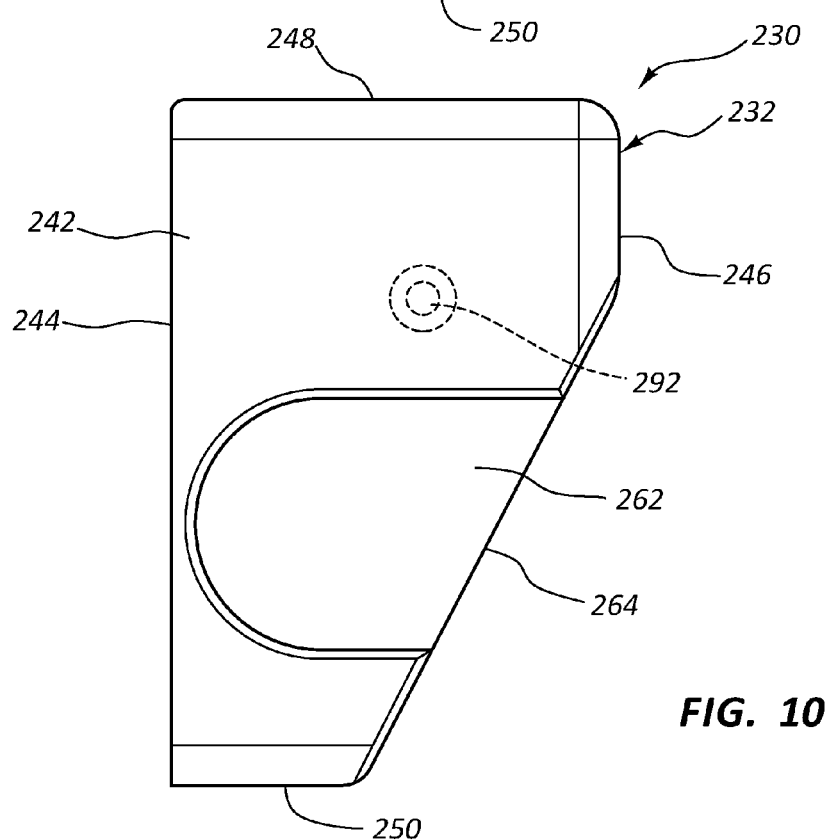
FIG. 10 is a left side view of the suture cutting device of FIG. 6.
Figure 11:
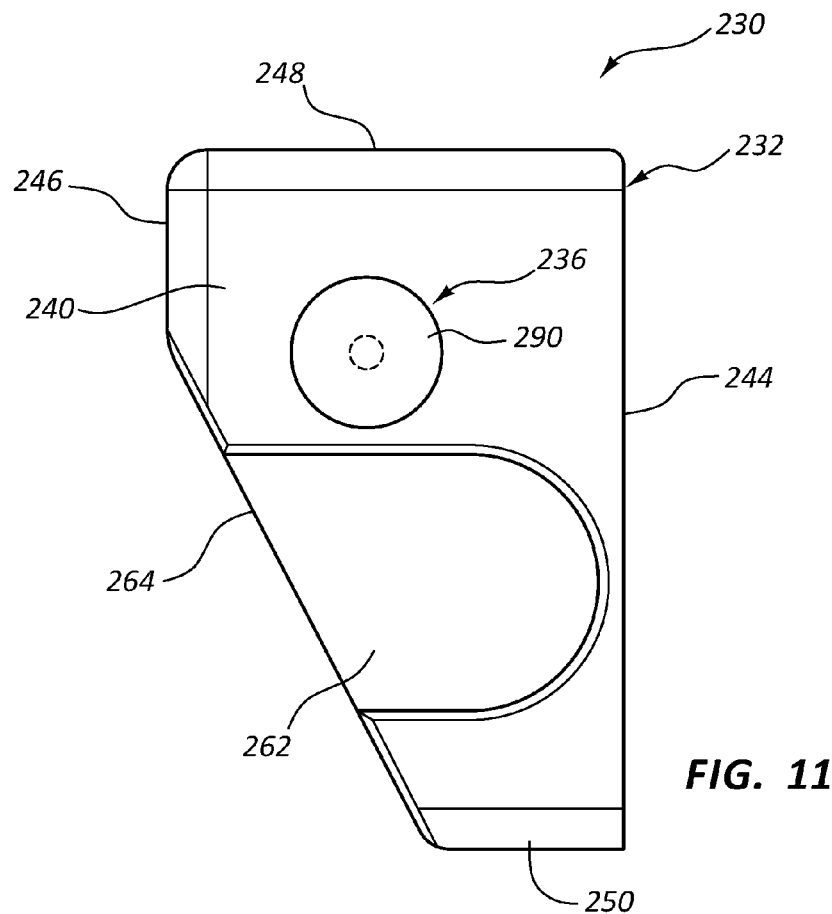
FIG. 11 is right side view of the suture cutting device of FIG. 6.
Figure 12:
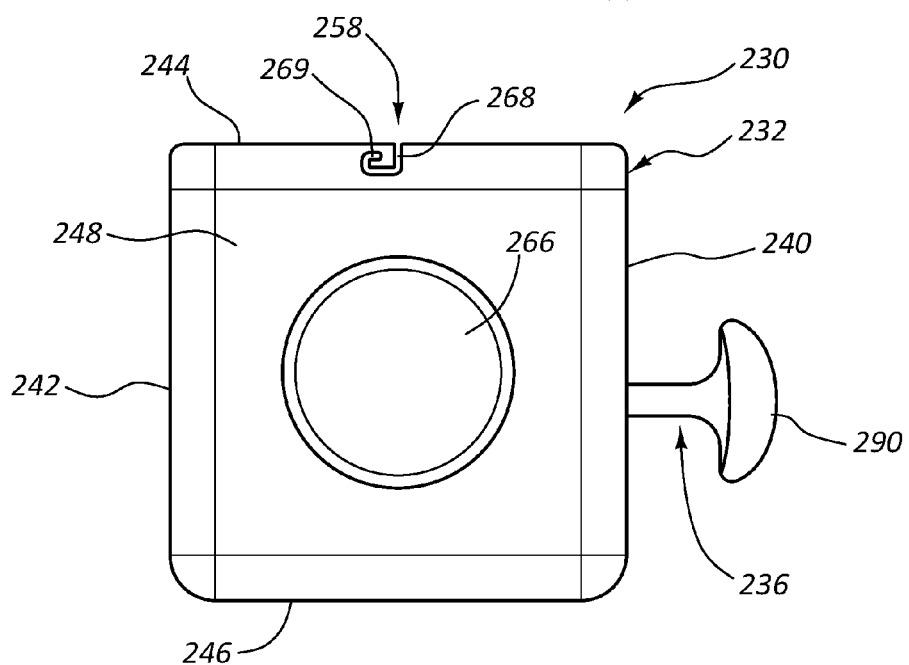
FIG. 12 is a top view of the suture cutting device of FIG. 6.
Figure 13:
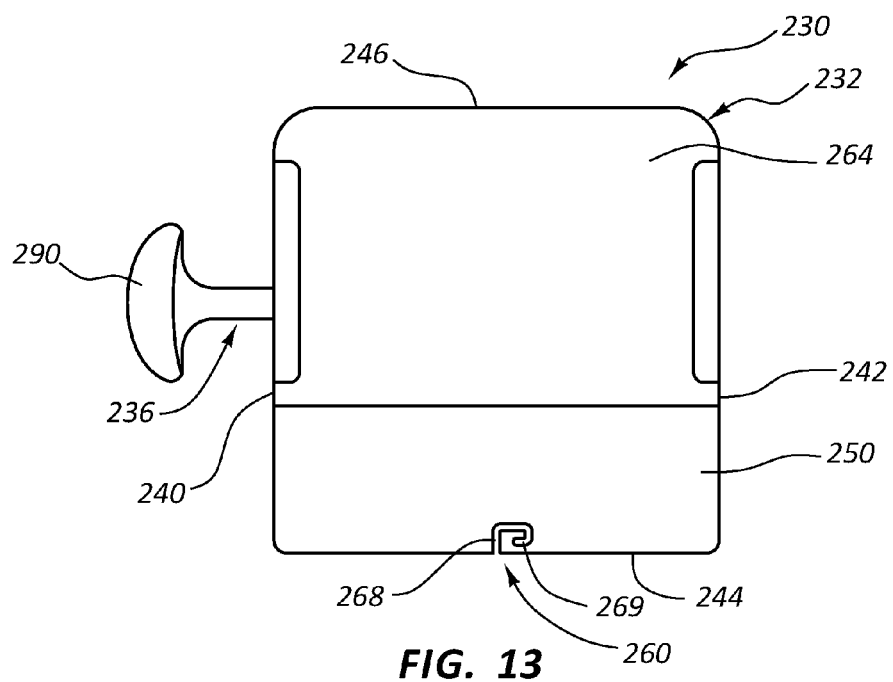
FIG. 13 is a bottom view of the suture cutting device of FIG. 6.

The actuator assembly 236 may include an actuator 290, an axle 292, a biasing member housing 294, a biasing member 296, a position stop 298 and a spacer 291. The actuator 290 extends through the first side 240 of the housing 232, and a distal end 293 of the axle 292 extends into the biasing member housing 294 (see FIG. 7). The distal end 293 may contact the biasing member 296. The biasing member 296 may bias the cutting member assembly 234 toward the first side 240 into a first or rest position shown in FIG. 7. Operating the actuator 290 in a lateral direction L as shown in FIG. 8 may load the biasing member 296 and move the cutting member assembly 234 in the lateral direction L. The cutting member assembly 234 may be fixed to the axle 292. In some arrangements, at least the position stop 298 is fixed to the axle 292.

Moving the cutting member assembly 234 moves the cutting member 270 past the second suture recess 260 to cut a suture passing through the housing 232. After releasing the force applied to actuator 290 in the direction L, the biasing member 296 may automatically move the cutting member assembly 234 in a reverse direction toward the first side 240. The position stop 298 may be mounted to the axle 292 between the cutting member assembly 234 and the first side 240. The position stop 298 may define an axial position of the cutting member assembly 234 relative to the first side 240.

The operation of actuator assembly 236 may be limited solely in the lateral direction L across a width W of the housing 232 (see FIG. 8). Other embodiments are possible in which the actuator assembly 236 operates to move the cutting member assembly 234 in other directions in addition to direction L. For example, the actuator assembly may operate to move the cutting member in a lateral direction across the width W as well as in a forward direction toward and away from the front side of the housing, or vertically up and down toward the bottom end of the housing while also moving laterally. In other embodiments, the cutting member assembly is movable in directions other than direction L.

Figure 14:
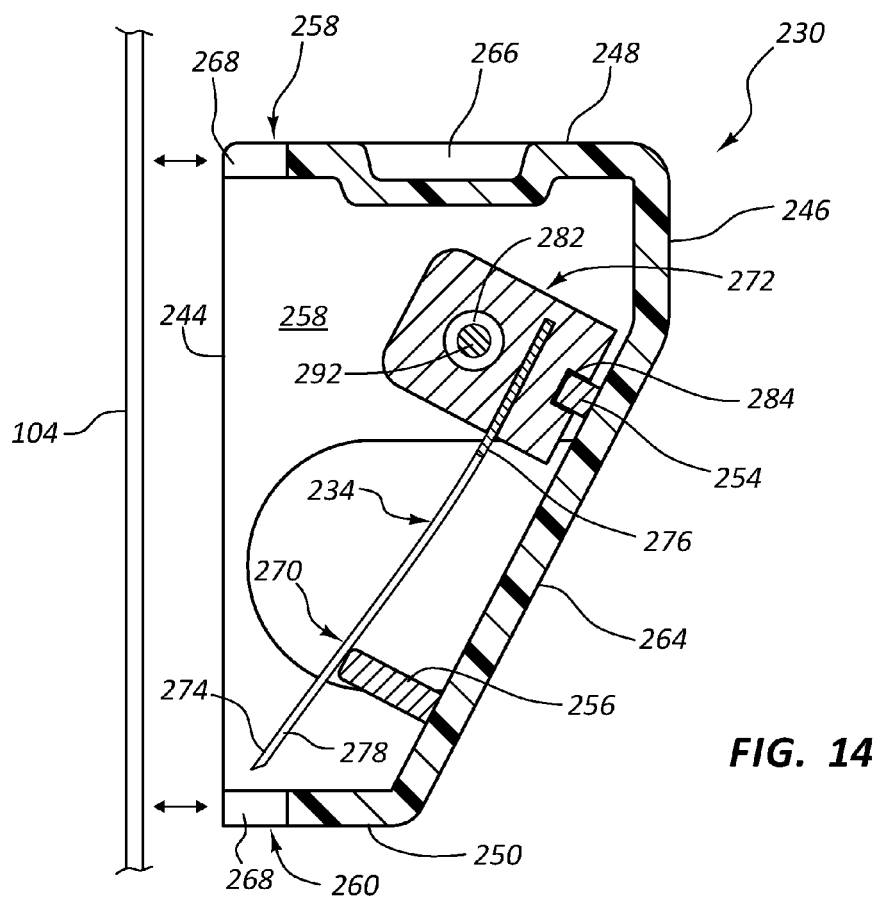
FIG. 14 is a cross-sectional view of the suture cutting device of FIG. 6 arranged for mounting to a suture.
Figure 15:
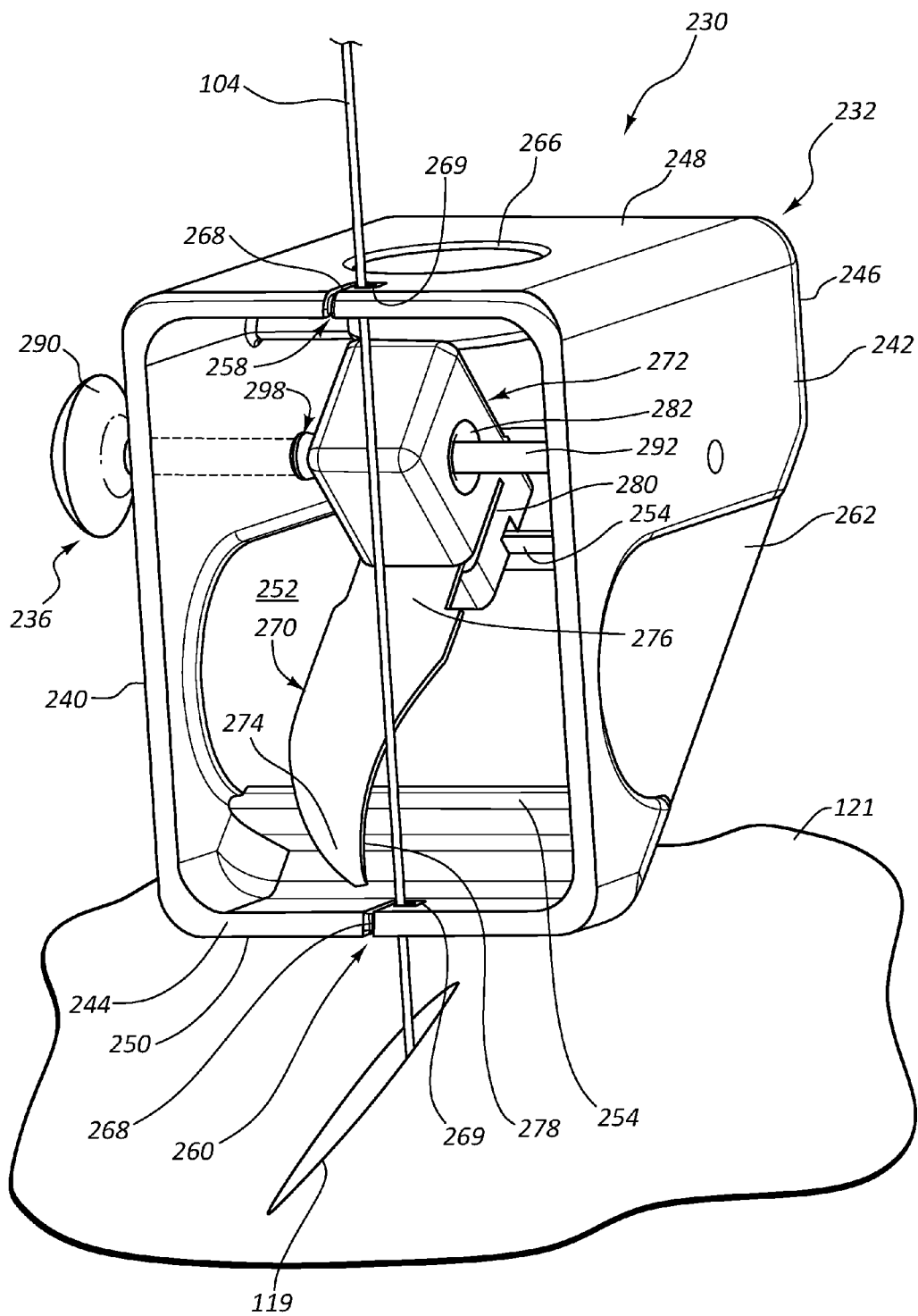
FIG. 15 is a perspective view of the suture cutting device of FIG. 6 mounted to the suture.
Figure 16:
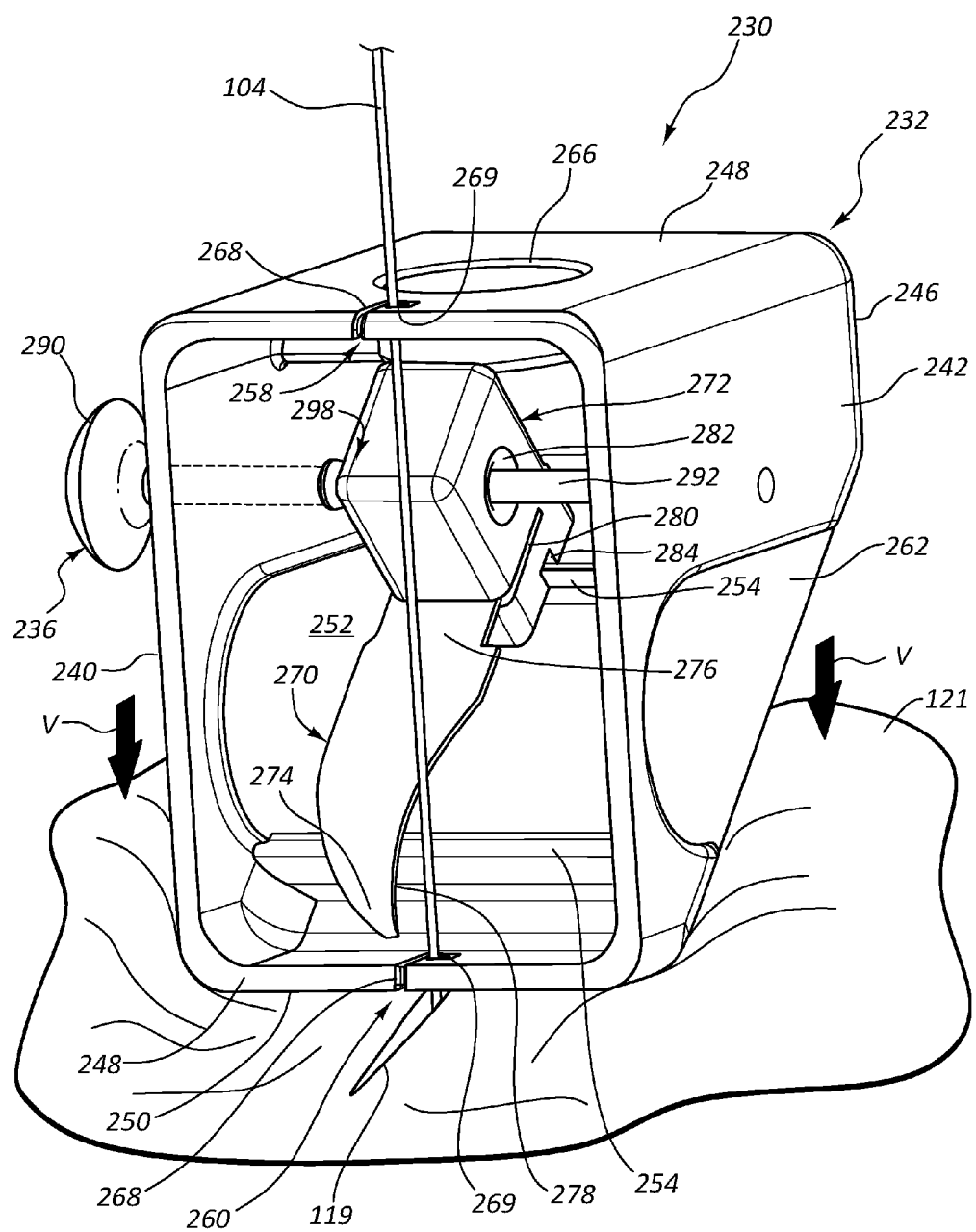
FIG. 16 shows the suture cutting device of FIG. 15 pressing down an outer skin surface of a patient.

Referring now to FIGS. 14-19, an example method of cutting a suture using the suture cutting device 230 is shown and described. FIG. 14 shows the suture cutting device 230 in cross-section and positioned laterally adjacent to a suture 104. The suture 104 is inserted into the first and second suture recesses 258, 260 in a lateral direction and retained within the retention portion 269 as shown in FIG. 15. The suture cutting device 230 may slide along the suture 104 and into contact with an outer skin surface 121 adjacent to a percutaneous incision 119. The operator may apply a downward directed force in a vertical direction V (e.g., a direction perpendicular to the outer skin surface 121) as shown in FIG. 16 to press the housing 232 against the outer skin surface 121. This application of force usually compresses the tissue layer such that a portion of a suture 104, which is typically positioned within the percutaneous incision 119, is then exposed within the interior 252 of housing 232, as shown in FIG. 16.

Figure 17:
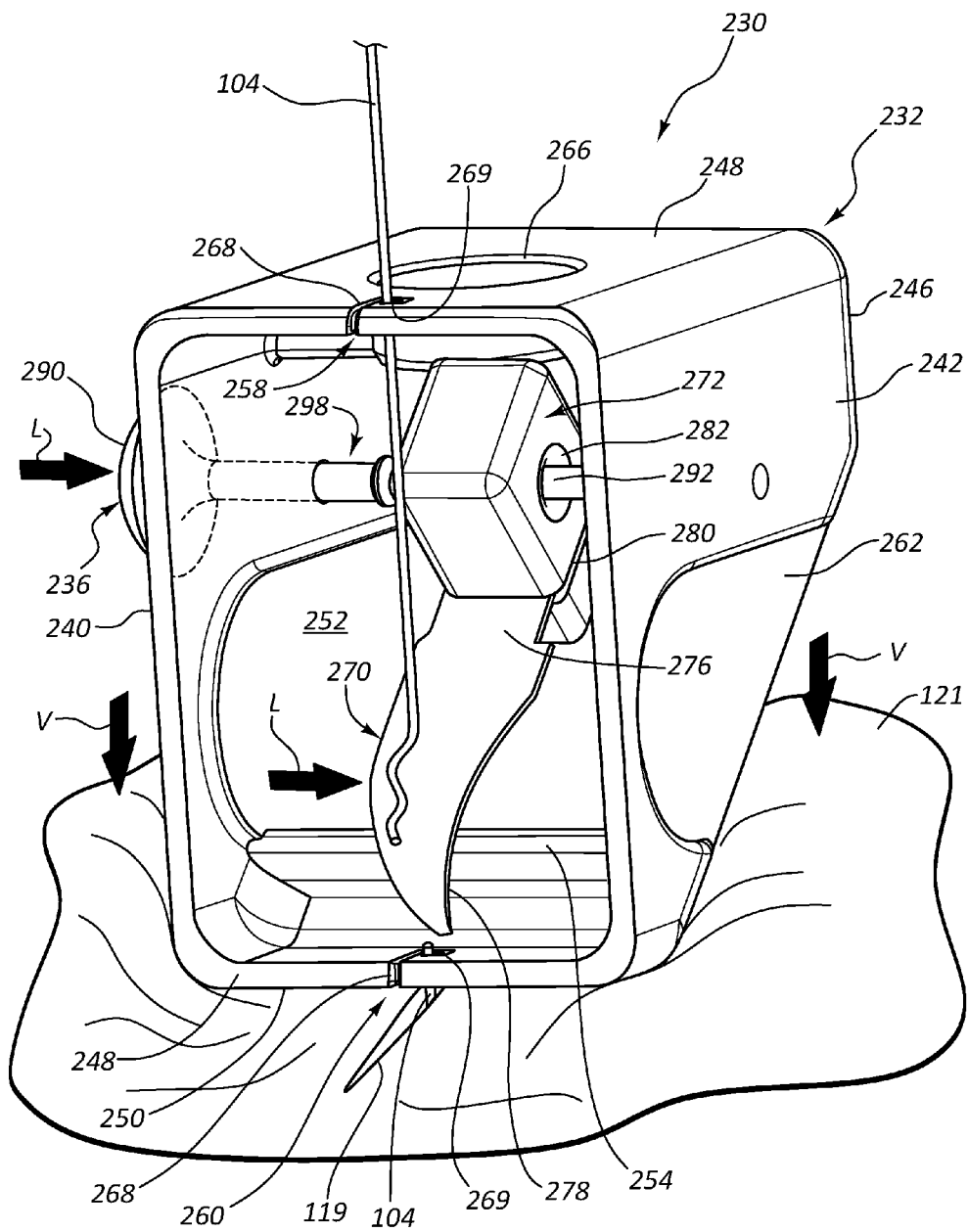
FIG. 17 shows the suture cutting device of FIG. 15 operated to cut the suture.

The operator may then apply a force to the actuator 290 in a lateral direction L while maintaining the downward applied force in a vertical direction V to move the cutting member assembly 234 within the interior 252 of housing 232 as shown in FIG. 17. The cutting member 270 contacts the suture 104 along the cutting surface 278 to cut the suture 104 as shown in FIG. 17. Thereafter, the operator releases the downward directed force such that the outer skin surface 121 may rebound to its original, uncompressed state prior to being contacted with the suture cutting device 230.

Figure 18:
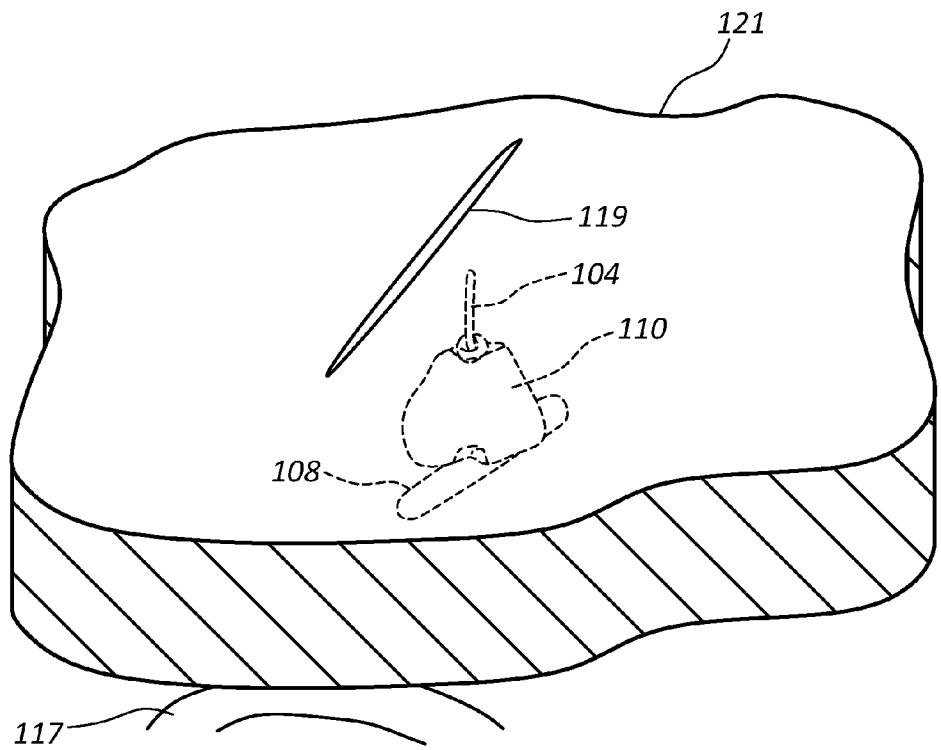
FIG. 18 is a perspective view showing a free end of the cut suture positioned below the outer skin surface of a patient.
Figure 19:
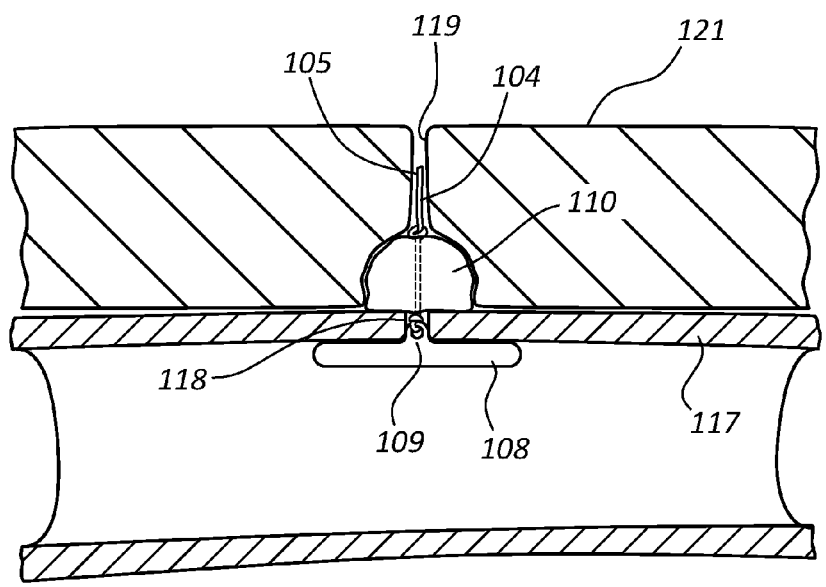
FIG. 19 is a side view of the cut of FIG. 18.

The cut suture 104 is shown in FIG. 18 positioned below the outer skin surface 121 with its cut end 105 positioned within the percutaneous incision 119. FIG. 19 is a side view showing the cut end 105 of suture 104 positioned within the percutaneous incision 119 and below the outer skin surface 121. The suture 104 is cut to a length that provides complete positioning of the suture 104 within the patient (i.e., within the percutaneous incision 119) while minimizing exposure of the patient (e.g., the outer skin surface 121 and percutaneous incision 119) to the cutting member 270. The cutting of suture 104 with a cutting member 270 may occur within the interior 252 of housing 232 at a location that is isolated from the patient using at least the bottom end 250 of the housing 232.

The suture cutting device 230 may be operable with a single hand of the operator. The other hand of the operator may be free to apply tension to suture 104 while mounting the suture cutting device 230 to the suture 104, applying a compression force to the outer skin surface 121 with the housing 232, and operating the actuator assembly 236 to cut the suture 104 with the cutting member 270.

The suture cutting device 230 may replicate the action of doctors using a hemostat and razor blade to cut the suture below the skin. However, the suture cutting device disclosed herein may minimize or even eliminate the potential for cutting either the patient or the operator who is cutting the suture. The suture cutting device may also minimize or substantially eliminate any potential need to excessively tension the suture prior to cutting the suture, which minimizes the risk of tearing the sealing plug or dislodging the anchor during cutting of a suture.

The structure and operation of the suture cutting device may make it possible to avoid applying excessive tension in the suture during cutting by applying an opposite downward directed pressure on the outer skin surface adjacent to the suture and percutaneous incision. As such, the operator may rely at least in part on pushing the skin downward rather than only applying tension force in the suture in order to optimize the ease of cutting and provide cutting below the outer skin surface.

The suture cutting devices disclosed herein may also reduce or at least standardize the amount of time required to cut the suture. The steps of mounting the suture cutting device to the suture, advancing the suture cutting device along the length of the suture to the outer skin surface, applying a downward compressive force to the outer skin surface with the suture cutting device, and operating the actuator assembly to move the cutting member within the housing to cut the suture may be relatively simple, straightforward, and easily repeatable steps for cutting a suture.

Furthermore, the suture cutting device disclosed herein may simplify the procedure for cutting a suture by integrating the cutting and compressing features into a single device. The housing of the suture cutting device may be used as a compressive device to compress the outer skin surface adjacent to the suture. The suture cutting device includes a cutting member and actuator integrated into or at least mounted to a common housing such that the entire device may be held in and operated by a single hand of the operator.

Furthermore, the suture cutting device disclosed herein may substantially limit the risk of cutting the patient or the operator with the cutting member of the suture cutting device prior to, during and after operation of the suture cutting device to cut the suture.

The preceding description has been presented only to illustrate and describe exemplary embodiments of the present disclosure. It is not intended to be exhaustive or to limit the invention to any precise form disclosed. Many modifications and variations are possible in light of the above teaching. It is intended that the scope of the invention be defined by the following claims.

What is claimed is:

1. A suture cutting device, comprising:
 a housing having an interior defined by at least four side walls;
 a blade positioned in the interior of the housing;
 a first suture recess and a second suture recess, the first and second suture recesses being formed in at least two of the at least four side walls of the housing, the first and second suture recesses being configured to releasably connect the housing to a suture, the blade being positionable between the first and second suture recesses;
 an actuator accessible outside of the housing and operable to move the blade laterally relative to the suture within the interior of the housing from a first position out of contact with the suture to a second position cutting the suture at a point on the suture, the point on the suture being positioned within the interior defined by the at least four side walls of the housing and positioned between the first and second suture recesses.

2. The suture cutting device of claim 1, wherein the blade is biased into the first position relative to the suture.

3. The suture cutting device of claim 1, wherein the blade comprises an elongate blade.

4. The suture cutting device of claim 1, wherein the blade has a contoured shape along its length.

5. The suture cutting device of claim 1, wherein the housing comprises a skin contact surface arranged to contact a skin surface through which the suture extends.

6. The suture cutting device of claim 1, wherein the housing has a tapered shape from a first end to a second end.

7. The suture cutting device of claim 1, wherein the actuator extends laterally from a sidewall of the housing.

8. The suture cutting device of claim 1, wherein the blade is arranged in the housing at an angle relative to the suture.

9. A suture cutting device, comprising:
 a housing comprising:
  a housing interior;
  a first suture recess and a second suture recess, each of the first and second suture recesses comprising an entry portion and a retention portion that extend along the housing in different directions relative to each other, the first and second suture recesses being configured to releasably connect the housing to a suture with the suture passing through the housing interior and the retention portions of the first and second suture recesses;
 a cutter positionable between the first and second suture recesses;
 an actuator coupled to the cutter and operable to move the cutter within the housing interior to cut the suture at a contact position on the suture, the contact position on the suture being positioned within the housing interior and being positioned between the first and second suture recesses.

10. The suture cutting device of claim 9, wherein the housing includes opposing first and second end walls, and at least one of the first and second suture recesses is formed in at least one of the first and second end walls.

11. The suture cutting device of claim 10, wherein the at least one suture recess is open in a lateral direction.

12. The suture cutting device of claim 10, wherein the first suture recess is formed in the first end wall and the second suture recess is formed in the second end wall.

13. The suture cutting device of claim 9, wherein the cutter comprises an elongate blade movable in a lateral direction relative to the suture.

14. The suture cutting device of claim 13, wherein the actuator includes a first portion accessible along an exterior of the housing and a second portion coupled to the blade to move the blade along an axle within the housing.

* * * * *